United States Patent
Leedham et al.

(10) Patent No.: US 11,484,639 B2
(45) Date of Patent: Nov. 1, 2022

(54) CLIP

(71) Applicant: Multigate Medical Products Pty Ltd, Villawood (AU)

(72) Inventors: Amy Leedham, Villawood (AU); Daniel Macks, Villawood (AU)

(73) Assignee: MULTIGATE MEDICAL PRODUCTS PTY LTD, Villawood (AU)

( * ) Notice: Subject to any disclaimer, the term of this patent is extended or adjusted under 35 U.S.C. 154(b) by 0 days.

(21) Appl. No.: 17/430,828

(22) PCT Filed: Feb. 14, 2020

(86) PCT No.: PCT/AU2020/000014
§ 371 (c)(1),
(2) Date: Aug. 13, 2021

(87) PCT Pub. No.: WO2020/163895
PCT Pub. Date: Aug. 20, 2020

(65) Prior Publication Data
US 2022/0040397 A1 Feb. 10, 2022

(30) Foreign Application Priority Data
Feb. 15, 2019 (AU) .................. 2019100169

(51) Int. Cl.
*A61M 1/00* (2006.01)
(52) U.S. Cl.
CPC .................... *A61M 1/774* (2021.05)
(58) Field of Classification Search
CPC .............. A61M 1/774; A61M 2209/06; B65D 63/1018; B65D 63/109; B65D 67/00; B65D 67/02; Y10T 24/12; Y10T 24/1406; Y10T 24/1604; A61B 2090/038
See application file for complete search history.

(56) References Cited

U.S. PATENT DOCUMENTS

| 4,212,300 A | 7/1980 | Meals |
| 4,759,349 A * | 7/1988 | Betz ..................... A61M 5/1483 604/27 |
| 5,265,840 A * | 11/1993 | Gillespie ............. A61M 3/0208 251/4 |
| 6,115,891 A | 9/2000 | Suenaga et al. |

(Continued)

FOREIGN PATENT DOCUMENTS

WO 8404684 A1 12/1984

OTHER PUBLICATIONS

Int'l Search Report dated Mar. 16, 2020 in Int'l Application No. PCT/AU2020/000014.

(Continued)

*Primary Examiner* — Bhisma Mehta
*Assistant Examiner* — John J Crawford
(74) *Attorney, Agent, or Firm* — Panitch Schwarze Belisario & Nadel LLP

(57) ABSTRACT

A clip for holding one or more buttons of a medical device in a pre-use state. The clip includes an elongate band for wrapping around the medical device. A receiving portion formed in the elongate band that is configured to receive at least one button when the band is wrapped around the medical device and a retaining means for retaining the band around the medical device.

5 Claims, 2 Drawing Sheets

(56) References Cited

U.S. PATENT DOCUMENTS

| | | | |
|---|---|---|---|
| 2009/0106948 A1* | 4/2009 | Lopez | B65D 63/1018 24/16 PB |
| 2014/0207056 A1* | 7/2014 | Bono | A61M 1/7411 604/34 |
| 2018/0177954 A1 | 6/2018 | Lee | |
| 2018/0327156 A1* | 11/2018 | Gupta | B65D 63/1018 |

OTHER PUBLICATIONS

Int'l Preliminary Report on Patentability dated Apr. 23, 2021 in Int'l Application No. PCT/AU2020/000014.

* cited by examiner

CLIP

TECHNICAL FIELD

The present invention relates to a clip. According to one particular example, the present invention relates to a clip which is used to keep a medical device, such as a suction/irrigator, in a pre-use condition such that the device can be stored and transported as required.

BACKGROUND OF THE INVENTION

The following references to and descriptions of prior proposals or products are not intended to be and are not to be construed as, statements or admissions of common general knowledge in the art. In particular, the following prior art discussion does not relate to what is commonly or well known by the person skilled in the art, but assists in the understanding of the inventive step of the present invention of which the identification of pertinent prior art proposals is but one part.

Often, sensitive medical equipment needs to be transported and stored for a period of time, before being used. It is thus often necessary to maintain the medical device in a pre-use state whilst the device is being transported/stored to maximise the device's integrity or to limit any alterations to the device that can affect its use. A particular example of a medical device where it is important to maintain the integrity of the internal tubing mechanism is a suction/irrigation device.

It will be appreciated by persons skilled in the art that the clip can be sterile or non-sterile. Further, the clip can be formed from any suitable material, such as, for example, any type of polymer, such as, but not limited to Low-Density Polyethylene (LDPE).

The present invention seeks to provide a clip which may ameliorate the foregoing shortcomings and disadvantages or which will at least provide a useful alternative to maintaining a medical device in a pre-use state.

SUMMARY OF THE INVENTION

According to one aspect of the invention, there is provided herein a clip for holding one or more buttons of a medical device in a pre-use state or condition, the clip including: an elongate band for wrapping around the medical device; a receiving portion formed in the elongate band, the receiving portion being configured to receive at least one button when the elongate band is wrapped around the medical device; and a retaining means for retaining the elongate band around the medical device.

According to one particular example, the medical device is a suction and/or irrigator apparatus/device, where one or more buttons are operatively connected to respective one or more suction/irrigation tubes or conduits of the suction/irrigator and formed such that in the pre-use state, the buttons can be held in a depressed state thereby holding the one or more tubes in an open state.

According to another aspect, there is provided herein a suction/irrigation clip, wherein in use, the clip holds one or more buttons of a suction/irrigation apparatus in a pre-use state, the clip including: an elongate band for wrapping around the suction/irrigation apparatus; a receiving portion formed in the elongate band, the receiving portion being configured to receive at least one button when the elongate band is wrapped around the suction/irrigator; and, a retaining means for retaining the elongate band around the suction/irrigation apparatus; wherein the one or more buttons are operatively connected to respective one or more suction/irrigation tubes of the suction/irrigator and formed such that the pre-use state allows for the buttons to be held in a depressed state such that one or more tubes are held in an open state.

It will be appreciated by persons skilled in the art that holding the tubes/conduits in an open, pre-use state can allow for integrity of the tubes to be maintained, before the device is used. That is, as the tubes are typically biased in a closed position, by maintaining the tubes in an open position (state or configuration), can allow for the tubes to be closed only in use. Thus, as the tubes are not deformed prior to use, it will be appreciated that in use, once the tubes are closed and opened by pressing the buttons of the device, this can provide improved fluid flow.

An example of a suction/irrigator device where the clip as described herein can be used with is shown in WO2017/219070 "Suction and Irrigation Apparatus", and further in AU2019100171 "A Pinch Valve Mechanism", the entire contents of all of which are incorporated herein.

According to one particular example, the receiving portion includes a raised portion, being raised from the elongate band such that a gap is formed between the raised portion and the band, thereby splitting the receiving portion into a first portion and a second portion. The first portion is typically raised in respect of the second portion and receives a first button and the second portion receives a second button, as the second button being offset from the first button.

It will be appreciated that if the buttons are not offset from one another, then the first portion and second portions can still be formed but may not necessarily be offset or raised in respect of each other. Further, the receiving portion may not necessarily have a gap forming the two portions but can also hold both buttons with one integrated portion.

According to yet another example, the retaining means includes one or more snap buttons. However, it will be appreciated by persons skilled in the art that the retaining means can include other type of fasteners such as clip buttons, or hook and loop fastening devices, or the like.

In yet a further example, the elongate band has a pull-tab for opening/releasing the band from being wrapped around the medical device. The pull-tab can be any form of tab, and can be disposed at an end of the elongate band or can be an extension of the elongate band.

According to another aspect, there is provided herein an apparatus or device for suction/irrigation, the device including: a suction/irrigator for performing suction/irrigation, the suction/irrigator having one or more buttons being operatively connected to respective one or more suction/irrigation tubes of the suction/irrigator; and, a clip for holding the one or more buttons of the suction/irrigator in a pre-use state, the clip including: an elongate band for wrapping around the suction/irrigator; a receiving portion formed in the elongate band, the receiving portion being configured to receive at least one button when the elongate band is wrapped around the suction/irrigator; and, a retaining means for retaining the elongate band around the suction/irrigator.

It will be appreciated by persons skilled in the art that any combination of features described herein is possible.

BRIEF DESCRIPTION OF THE DRAWINGS

The invention may be better understood from the following non-limiting description of a preferred embodiment, in which.

DETAILED DESCRIPTION OF THE DRAWINGS

Figure 1:
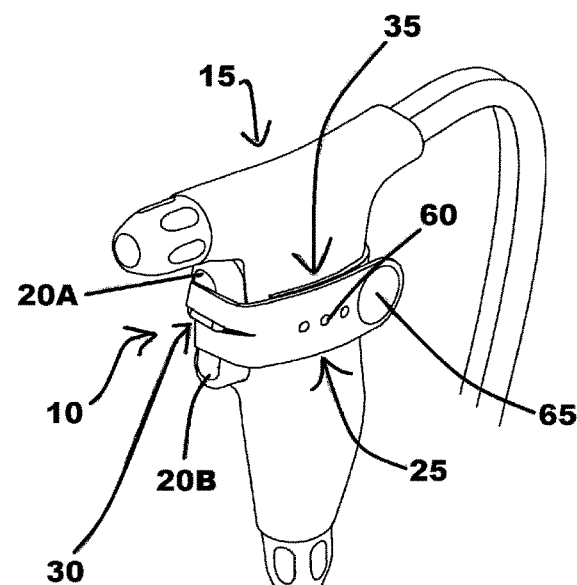
FIG. 1 is a perspective view of an example of a clip, in use with a suction/irrigator.
Figure 2:
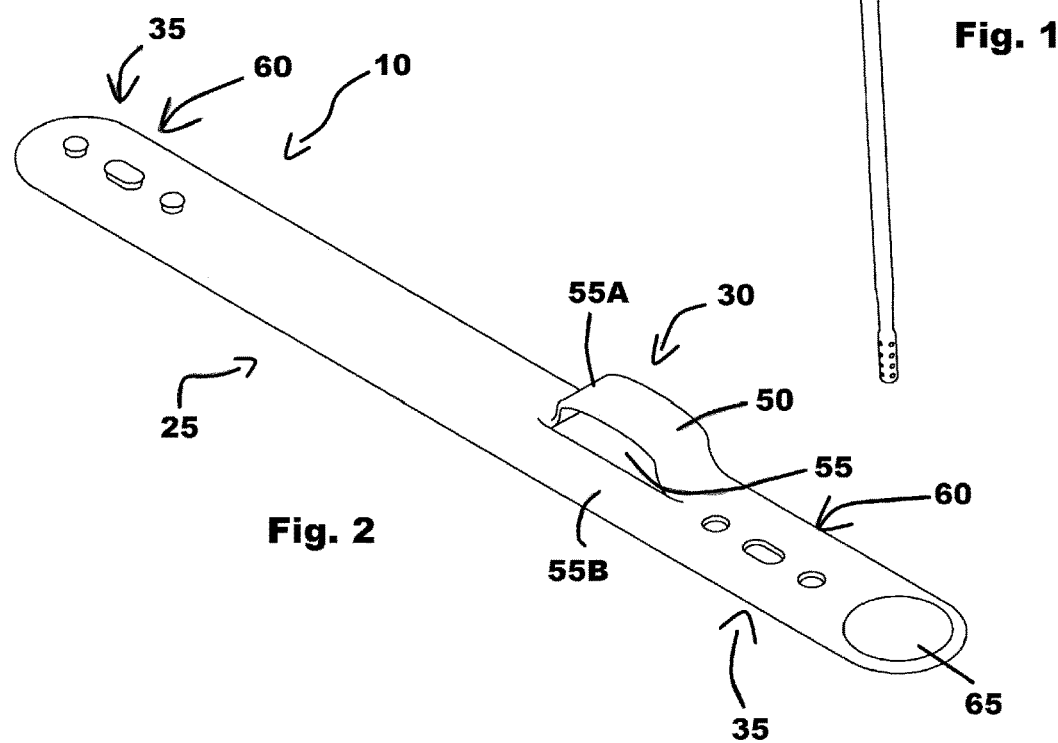
FIG. 2 is a perspective view of an example clip in open formation or not in use with a medical device; and, FIG. 3 is a side internal view of a suction/irrigator medical device that can benefit from the use of the clip of FIGS. 1 and 2.

An example of a clip 10 is shown in FIGS. 1 and 2.

According to a particular example, as shown in FIG. 1, a clip 10 can be used for holding one or more buttons 20A, 20B, of a medical device 15, in a pre-use state.

As shown in both FIGS. 1 and 2, the clip 10 includes an elongate band 25 for wrapping around the medical device 15. The clip 10 further includes a receiving portion which is configured to receive at least one button 20A/20B when the band 25 is wrapped around the medical device 15.

In addition to this, the clip 10 can include a retaining means 35 for retaining the band 25 around the medical device 15.

In this particular example, the medical device 15 is an apparatus or device for providing suction/irrigation to a body site (referred to herein as a suction/irrigator). However, it will be appreciated that the clip 10 is not limited to the use of keeping a suction/irrigator in a pre-use state or condition.

Figure 3:
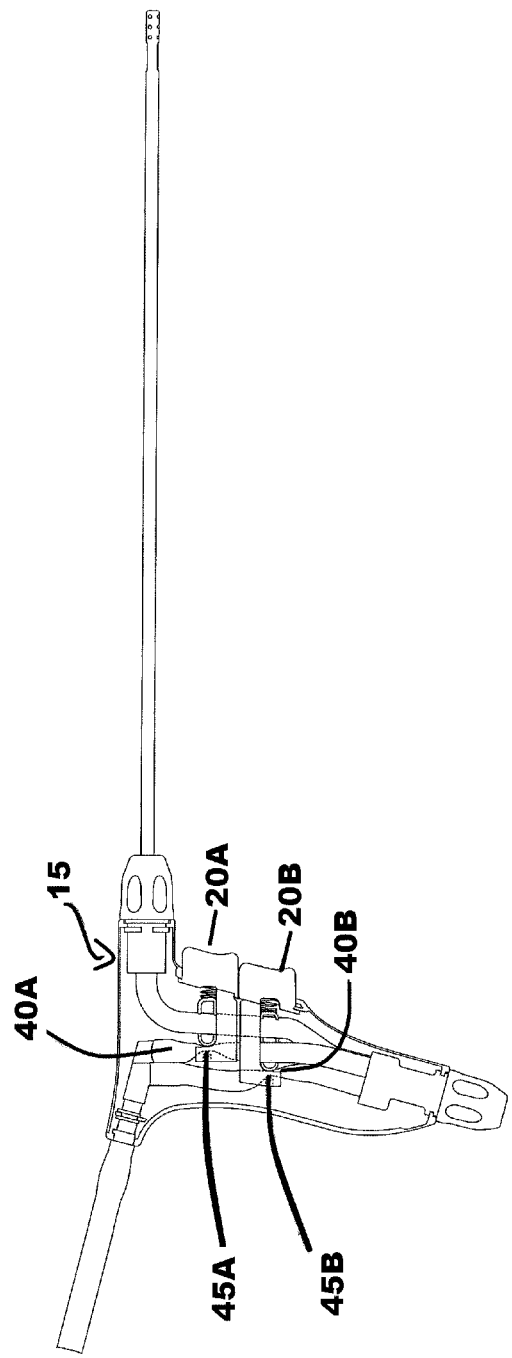

When used with a suction/irrigator, the one or more buttons 20A/20B are typically operatively connected to respective one or more suction/irrigation tubes 40A/40B of the suction/irrigator, as shown in FIG. 3. In this example, depression of the buttons 20A/20B, keep the respective tubes 40A/40B of the suction/irrigator 15 open as depression of the buttons 20A/20B forces a respective pinch valve 45A/45B to release the respective tube 40A/40B and thus open the tube. Accordingly, the pre-use state of the suction/irrigator 15 is that the tubes 40A/40B are held open in order to minimise any bending of the tubes (and thus affect the suction/irrigation function of the medical device 15 when the device 15 is used) whilst the suction/irrigator is in storage or being transported. It will be appreciated that this can allow for the integrity of the tubes to be maintained until the suction/irrigator 15 needs to be used and the clip 10 is opened, thereby returning the buttons 40A/40B to their biased closed state. Thus, the clip 10 pushes against the buttons 20A/20B to keep the tubes 40A/40B of the suction irrigator open.

According to one particular example, as shown in FIGS. 1 and 2, the receiving portion 30 includes a raised portion 50, being raised from the elongate band 25 such that a gap 55 is formed between the raised portion 50 and the band 25, thereby splitting the receiving portion 30 into a first receiving portion 55A and a second receiving portion 55B. In this particular example, the receiving portion 30 is configured to receive/hold two buttons 20A/20B, which are formed such that they are slightly offset from one another (as shown in FIG. 3). Thus, the first portion 55A is raised in respect of the second portion 55B such that the first portion 55A is configured to receive a first button 20A and the second portion 55B receives a second button 20B, where the second button 20B is offset from the first button 20A.

According to a further example, the retaining means, which wraps around the medical device (such as around a handle of the suction/irrigator) includes one or more snap buttons 60 to thereby hold the elongate band 25 wrapped around the device 15. It will be appreciated that although, the clip 10 includes 3 snap-button formations (with respective male/female parts), disposed at the ends of the elongate band, other fastening means of the elongate band may also be used. Further, there may be any number of buttons/snap-buttons or the like, in any shape or form.

In yet a further example, the clip 10 can have an elongate band, which has a pull-tab 65 disposed or formed on an end of the elongate band 25 for opening/releasing the band 25 from being wrapped around the medical device 15. That is, the pull-tab 65 once pulled can unlock the releasing means, thereby releasing the clip from the device. In this example, the pull-tab 65 is formed at an obround end of the elongate band 25, but it will be appreciated that the pull-tab 65 can be of any suitable shape.

Thus, it will be appreciated by persons skilled in the art that the clip as described herein can be used to hold a medical device in a pre-use state or condition, which can allow for the medical device to be transported or stored, whilst substantially maintaining the integrity of the device before use. Accordingly, the clip can ensure that once the clip is opened and that the device is ready for use, the effectiveness of the device has not been substantially affected by storage or transportation of the device.

It will be appreciated that whilst the clip described herein can be formed of any suitable material, it is likely to be formed from any type of polymer, such as, but not limited to Low-Density Polyethylene (LDPE).

The term "comprise" and variants of that term such as "comprises" or "comprising" are used herein to denote the inclusion of a stated integer or integers but not to exclude any other integer or integers, unless in the context or usage an exclusive interpretation of the term is required.

Those skilled in the art will appreciate that the invention described herein is susceptible to variations and modifications other than those specifically described. All such variations and modifications are to be considered within the scope and spirit of the present invention the nature of which is to be determined from the foregoing description.

The invention claimed is:

1. A suction/irrigation clip, wherein in use, the clip holds one or more buttons of a suction/irrigation apparatus in a pre-use state, the clip including:
   a. an elongate band for wrapping around the suction/irrigation apparatus;
   b. a receiving portion formed in the elongate band, the receiving portion being configured to receive the one or more buttons when the elongate band is wrapped around the suction/irrigator apparatus; and,
   c. a retaining means for retaining the elongate band around the suction/irrigation apparatus;
   wherein the one or more buttons are operatively connected to respective one or more suction/irrigation tubes of the suction/irrigator apparatus and formed such that the pre-use state allows for the one or more buttons to be held in a depressed state such that the one or more tubes are held in an open state, wherein the receiving portion includes a raised portion, being raised from the elongate band such that a gap is formed between the raised portion and the band, thereby splitting the receiving portion into a first receiving portion and a second receiving portion, where the first portion is raised in respect of the second portion and receives a first button of the one or more buttons and the second portion receives a second button of the one or more buttons, the second button being offset from the first button.

2. The clip of claim 1, wherein the retaining means includes one or more snap buttons to hold the elongate band around the suction/irrigation apparatus.

3. The clip of claim 1, wherein the elongate band has a pull-tab for opening/releasing the band from being wrapped around the suction/irrigation apparatus.

4. The clip of claim 3, wherein the pull-tab is formed at an obround end of the elongate band.

5. A device for suction/irrigation, the device including:
   a suction/irrigation apparatus having one or more buttons being operatively connected to respective one or more suction/irrigation tubes of the suction/irrigation apparatus; and
   a clip for holding the one or more buttons of the suction/irrigation apparatus in a pre-use state, the clip including:
   a. an elongate band for wrapping around the suction/irrigation apparatus;
   b. a receiving portion formed in the elongate band, the receiving portion being configured to receive the one or more buttons when the elongate band is wrapped around the suction/irrigation apparatus; and,
   c. a retaining means for retaining the elongate band around the suction/irrigation apparatus, wherein the receiving portion includes a raised portion, being raised from the elongate band such that a gap is formed between the raised portion and the band, thereby splitting the receiving portion into a first receiving portion and a second receiving portion, where the first portion is raised in respect of the second portion and receives a first button of the one or more buttons and the second portion receives a second button of the one or more buttons, the second button being offset from the first button.

\* \* \* \* \*